United States Patent [19]
Takahashi et al.

[11] Patent Number: 6,126,940
[45] Date of Patent: *Oct. 3, 2000

[54] HAIR-GROWING AGENT COMPRISED OF PROANTHOCYANIDINS

[75] Inventors: Tomoya Takahashi, Tsuchiura; Yoshinori Kobayashi, Tsukuba; Michio Kawamura, Hofu; Yoshiharu Yokoo, Ushiku; Toshikazu Kamiya, Machida; Tatsuya Tamaoki, Machida, all of Japan

[73] Assignee: Kyowa Hakko Kogyo Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,634

[22] PCT Filed: Jun. 30, 1995

[86] PCT No.: PCT/JP95/01308

§ 371 Date: Dec. 30, 1996

§ 102(e) Date: Dec. 30, 1996

[87] PCT Pub. No.: WO96/00561

PCT Pub. Date: Jan. 11, 1996

[30] Foreign Application Priority Data

Jun. 30, 1994 [JP] Japan ..................................... 6-149681
Jul. 25, 1994 [JP] Japan ..................................... 6-172700

[51] Int. Cl.$^7$ .............................. A61K 7/06; A61K 35/78
[52] U.S. Cl. ........................ 424/195.1; 514/880; 514/456
[58] Field of Search .............................. 424/195.1, 78.08; 514/880

[56] References Cited

U.S. PATENT DOCUMENTS

| | | | |
|---|---|---|---|
| 4,508,714 | 4/1985 | Lecic et al. | 424/195.1 |
| 4,517,175 | 5/1985 | Twabochi et al. | 424/70.14 |
| 4,530,829 | 7/1985 | Abe | 424/70.14 |
| 4,698,360 | 10/1987 | Masquelier . | |
| 5,470,874 | 11/1995 | Lerner | 514/474 |

FOREIGN PATENT DOCUMENTS

WO 93/24106  12/1993  WIPO .

*Primary Examiner*—Peter F. Kulkosky
*Attorney, Agent, or Firm*—Antonelli, Terry, Stout & Kraus, LLP

[57] ABSTRACT

A hair-growing agent comprising proanthocyanidin as the active ingredient. The present invention provides a hair-growing agent having strong pharmaceutical effects.

3 Claims, No Drawings

HAIR-GROWING AGENT COMPRISED OF PROANTHOCYANIDINS

TECHNICAL FIELD

The present invention relates to a hair-growing agent comprising proanthocyanidin as the active ingredient.

BACKGROUND ART

Tannin exists broadly in the plants and has many phenolic hydroxyl groups in the molecule. Tannin is classified into a hydrolyzable tannin that is hydrolyzed with acid, alkali or tannase, and a condensed tannin that is not hydrolyzed. It is known that the condensed tannin includes a simple condensed tannin (proanthocyanidin) which is composed of constitutive flavan-3-ol units and a complex condensed tannin which is composed of constitutive units of flavan-3-ol, caffeic acid and chalcone-$\beta$-ol.

It is known that such a condensed tannin has a hair-protecting effect (see Japanese Published Examined Patent Application No. 37884/90). However, the effect is exclusively exerted on the surface of hair as the effect of a cosmetic, and the hair-growing effect of the condensed tannin is unknown. Proanthocyanidin is utilized as an antioxidant (see Japanese Published Unexamined Patent Application No. 16982/86), but the hair-growing effect of proanthocyanidin is unknown.

DISCLOSURE OF THE INVENTION

The present invention relates to a hair-growing agent comprising proanthocyanidin as the active ingredient.

The present invention also relates to the use of proanthocyanidin in preparing a pharmaceutical composition for treating male pattern baldness (alopecia hereditaria). The present invention further relates to a method for treating male pattern baldness by the use of a pharmaceutical composition comprising proanthocyanidin as the active ingredient.

Proanthocyanidin indicates a group of polymer compounds composed of constitutive units of flavan-3-ol derivatives of a formula (I):

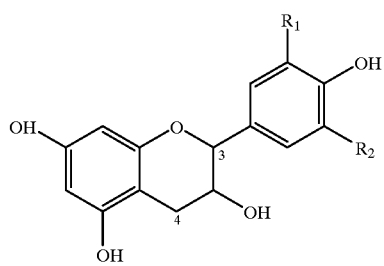

(I)

wherein $R_1$ and $R_2$ are the same or different and each represents a hydrogen atom or a hydroxyl group.

Examples of the flavan-3-ol derivatives of formula (I) include catechin, epicatechin, gallocatechin, epigallocatechin, afzelechin, epiafzelechin, etc., and include all their isomers. Proanthocyanidin composed of constitutive units of epicatechin or catechin is more preferably used in the hair-growing agent of the present invention.

Any bonding mode of flavan-3-ol polymers comprising the units of formula (I) is acceptable. For example, diners to be formed by polymerization of two flavan-3-ol units may have any bonding mode of a formula (II):

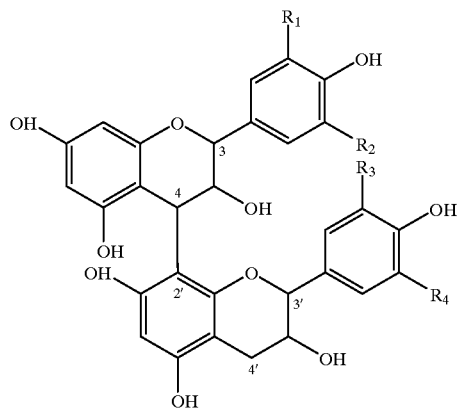

(II)

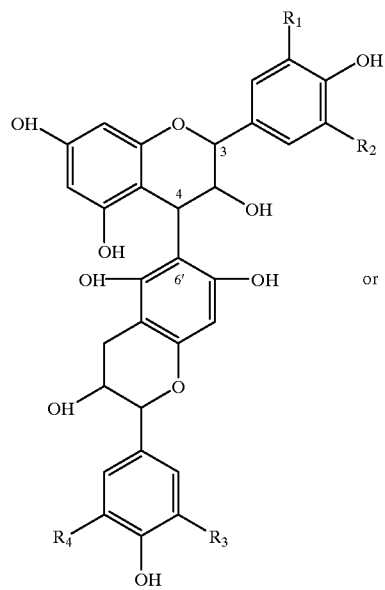

or

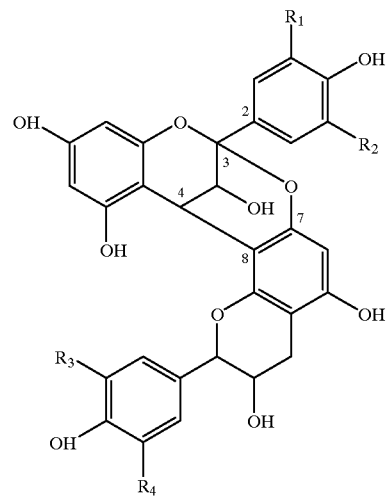

wherein $R_1$ and $R_2$ have the same meanings as defined above, and $R_3$ and $R_4$ are the same or different and each represents a hydrogen atom or a hydroxyl group. The same or different ones of such bonding modes are combined to give trimers and higher polymers.

Proanthocyanidin to be used in the present invention is a dimer or higher polymer composed of flavan-3-ol derivatives and is preferably a 2- to 10-mer, more preferably a 2- to 5-mer, even more preferably a dimer or trimer. Especially preferred examples of dimers of flavan-3-ol derivatives are epicatechin-catechin co-dimers such as epicatechin-(4β→8)-catechin, etc.; epicatechin dimers such as epicatechin-(4β→6)-epicatechin, epicatechin-(4β→8)-epicatechin, etc.; catechin dimers such as catechin-(4α→8)-catechin, etc. Especially preferred examples of trimers of flavan-3-ol derivatives are epicatechin trimers such as epicatechin-(4β→8)-epicatechin-(4β→8)-epicatechin, epicatechin-(4β→8)-epicatechin-(4β→6)-epicatechin, etc.; catechin trimers such as catechin-(4α→8)-catechin-(4α→8)-catechin, etc.; epicatechin-catechin co-trimers such as epicatechin-(4β→8)-epicatechin-(4β→8)-catechin, etc.

Proanthocyanidin can be extracted and purified from various plants such as grape, kaki (Japanese persimmon), betel palm, apple, barley, Nest-leaf, rhubarb, cinnamon, adzuki bean, raspberry, etc. In addition, it can also be obtained by chemical synthesis.

To extract and purify proanthocyanidin from such plants, any known method such as that mentioned below can been employed. Raw fruits, seeds, leaves, roots, rootstocks and other plants are harvested at suitable stages. These are used, directly or after having been dried by conventional air drying or the like, as raw materials to be extracted. Plant juice or milk may be directly used as a raw material to be extracted.

The extraction of proanthocyanidin from dry plants can be conducted with reference to known methods [see Chemical Pharmaceutical Bulletin, 38, 3218 (1990); ibid., 40, 889 (1992)]. The raw material is ground into powder or cut into fine pieces and is extracted batchwise or continuously with a solvent. The extraction solvent may be a hydrophilic or oleophilic solvent, including, for example, water, alcohols such as ethanol, methanol, isopropyl alcohol, etc., ketones such as acetone, methyl ethyl ketone, etc., esters such as methyl acetate, ethyl acetate, etc. These can be used singly or as mixed solvents. The extraction temperature is generally between 0° C. and 100° C., preferably between 5° C. and 50° C.

Where the extraction is conducted batchwise, the extraction time is from 1 hour to 10 days or so, the amount of the solvent is generally from 1 to 30 times by weight, preferably from 5 to 10 times by weight based on the dry raw material. The extraction may be effected either with stirring or by dipping. If desired, the extraction may be repeated two or three times. As the continuous extraction, for example, employable is a method of using a Soxhlet extractor comprising a reflux condenser and a siphon, in which the amount of the solvent, the extraction time and other conditions are the same as those in the above-mentioned batchwise extraction method.

From the crude extract as obtained in the manner mentioned above, removed are the insoluble residues by filtration or centrifugation. Proanthocyanidin is purified from the thus-treated extract by any known method of separating and purifying herb. It is preferable to employ a two-phase solvent partitioning method, a column chromatographic method and a partitioning high-performance liquid chromatographic method and the like, singly or as combined. The two-phase solvent partitioning method includes a method of extracting and removing the oil-soluble components and dyes from the above-mentioned extract by the use of n-hexane, petroleum ether or the like, a method of partitioning the extract into a solvent phase of n-butanol, methyl ethyl ketone or the like and collecting proanthocyanidin from the solvent phase, etc. The column chromatographic method includes an ion-exchange column chromatographic method of using Amberlite IR-120B, Amberlite IRA-402 or the like as the carrier, an adsorption column chromatographic method of using a normal phase silica gel, a reversed phase silica gel, Diaion HP-20, Sepabeads SP-207 or the like as the carrier, a gel permeation method of using Sephadex LH-20 or the like as the carrier, etc. These can be used singly or as combined for repeated systems. The partitioning high-performance liquid chromatographic method includes a method of using reversed phase columns filled with octadecyl silica or the like, a method of using normal phase columns filled with silica gel, silica gel-$NH_2$ or the like, etc.

As a result of the above-mentioned purification, water-soluble ionic substances such as salts, etc., non-ionic substances such as saccharides, polysaccharides, etc., oils, dyes, etc. are removed from the crude extract, and proanthocyanidin is obtained.

Regarding chemical synthesis of proanthocyanidin, a method of producing dimers of epicatechin or catechin is disclosed in Journal of Chemical Society, Parkin Transaction I, pp. 1535–1543, 1983. To chemically produce proanthocyanidin for use in the present invention, the method disclosed in the reference is referred to.

Where proanthocyanidin is used as the active ingredient in the present invention, one or more kinds of proanthocyanidin can be used singly or as mixtures.

The form of the hair-growing agent of the present invention may be taken any form, provided that it can contain proanthocyanidin as the active ingredient. A liquid or solid hair-growing agent comprising proanthocyanidin along with suitable pharmaceutical vehicles is used. The form of such a liquid or solid hair-growing agent includes liquid-type preparations such as hair liquid, hair tonic, hair lotion, etc., and solid-type preparations such as ointment, hair cream, etc. These can be prepared by adding proanthocyanidin to suitable vehicles followed by formulating them into preparations. The single or combined proanthocyanidin content of the hair-growing agent of the present invention is generally from 0.01 to 30% by weight (hereinafter referred to as %), preferably from 0.1 to 10%, more preferably from 0.5 to 10%.

As vehicles suitable for liquid-type preparations,. mentioned are any conventional ones which are generally used in ordinary hair-growing agents. For example, usable are pure water, ethanol, polyalcohols, oils, fats, etc. If desired, additives may be added to the preparations. As the polyalcohols, mentioned are glycerol, 1,3-butylene glycol, propylene glycol, etc. As the oils and fats, mentioned are wheat germ oil, tsubaki (camellia) oil, jojoba oil, olive oil, squalane, safflower oil, macadamia nut oil, avocado oil, hydrogenated soybean lecithin, etc.

As the additives, mentioned are fragrances, surfactants, microbicides, etc. If desired, antioxidants, ultraviolet absorbents, anti-inflammatory agents, refreshing agents, moisturizers, vitamins, herb extracts, etc. may also be added to the preparations.

As the fragrances, any ones that are generally used in cosmetics, etc. may be used.

As the surfactants, mentioned are polyoxyethylene (60) hydrogenated castor oil, polyoxyethylene (8) oleyl ether, polyoxyethylene (10) monooleate, polyoxyethylene (30) glyceryl monostearate, sorbitan monostearate, polyoxyethylene (20) sorbitan monooleate, sucrose fatty acid esters, hexaglycerin monolaurate, polyoxyethylene reduced lanolin, POE (25) glyceryl pyroglutamate isostearate, isostearyl N-acetylglutamine, etc.

As the microbicides, mentioned are hinokitiol, triclosan, chlorohexidine gluconate, phenoxyethanol, resorcinol, isopropylmethylphenol, azulene, salicylic acid, zinc pyrithione, etc.

As the antioxidants, mentioned are butylhydroxylanisole, gallic acid, propyl gallate, erysorbic acid, etc.

As the ultraviolet absorbents, mentioned are benzophenones such as dihydroxybenzophenone, etc.; melanin, ethyl para-aminobenzoate, 2-ethylhexyl para-dimethylaminobenzoate, cinoxate, 2-ethylhexyl para-methoxycinnamate, 2-(2-hydroxy-5-methylphenyl) benzotriazole, urocanic acid, fine particles of metal oxides, etc.

As the anti-inflammatory agents, mentioned are dipotassium glycyrrhetinate, allantoin, etc.

As the refreshing agent, mentioned are capsicum tincture, 1-menthol, etc. As the moisturizers, mentioned are pyrrolidone-carboxylic acid, sodium hyaluronate, chondroitin sulfuric acid, etc.

As the vitamins, mentioned are dl-$\alpha$-tocopherol acetate, dl-$\alpha$-tocopherol, vitamin E, benzyl nicotinate, D-pantothenyl alcohol, pantothenyl ethyl ether, biotin, pyridoxine hydrochloride, riboflavin, etc.

As the herb extracts, mentioned are Swertia herb extract, garlic extract, ginseng extract, aloe extract, etc.

Where the above-mentioned liquid-type preparations are used as spray, they may be combined with incombustible liquefied gas or the like.

As the vehicles for solid-type preparations, mentioned are vaseline, solid paraffin, vegetable oil, mineral oil, lanolin, wax, macrogol, etc. If desired, the above-mentioned additives, emulsifiers such as lecithin, etc., lower alcohols such as ethanol, isopropyl alcohol, etc. can be added thereto.

The dose of the hair-growing agent of the present invention varies, depending on the age, the weight and the condition of the person to which it is applied, the curing effect of the agent, the mode of administration, the treating time, etc. In general, the agent is endermically applied at a dose of from 0.1 to 600 mg/adult, preferably from 10 to 300 mg/adult, in terms of proanthocyanidin, once to several times a day.

BEST MODE OF CARRYING OUT THE INVENTION

Embodiments of the present invention are described concretely by means of the following examples, referential examples and test examples. Of the proanthocyanidins used in the following examples, epicatechin-(4$\beta$→8)-epicatechin [Compound 2] was produced according to the method described in Chemical Pharmaceutical Bulletin, 41, 1491 (1993) and ibid., 38, 3218 (1990); and epicatechin-(4$\beta$→6)-epicatechin [Compound 4] and epicatechin-(4$\beta$→8)-epicatechin-(4$\beta$→6)-epicatechin [Compound 8] were produced according to the method described in Chemical Pharmaceutical Bulletin, 40, 889 (1992). The other proanthocyanidins used in the examples were produced according to the methods of Referential Examples 1 to 5.

EXAMPLE 1

Seven kg of ethyl alcohol, 500 g of glycerol, 300 g of Compound 1 as obtained in Referential Example 1, and 50 g of isostearyl N-acetylglutamine were uniformly stirred and blended in 1600 g of pure water, whereby the solids were dissolved to prepare Solution A. Apart from this, 500 g of 1,3-butylene glycol and 50 g of POE (25) glyceryl pyroglutamate isostearate were uniformly stirred and blended to prepare Solution B. Solution B was added to Solution A with stirring and uniformly blended to prepare a hair-growing tonic (Composition 1) The above-mentioned operations were conducted all at room temperature.

EXAMPLE 2

The same process as in Example 1 was repeated, except that Compound 2 was used in place of Compound 1 as obtained in Referential Example 1, to prepare a hair-growing tonic (Composition 2).

EXAMPLE 3

The same process as in Example 1 was repeated, except that Compound 3 as obtained in Referential Example 2 was used in place of Compound 1 as obtained in Referential Example 1, to prepare a hair-growing tonic (Composition 3).

EXAMPLE 4

The same process as in Example 1 was repeated, except that Compound 4 was used in place of Compound 1 as obtained in Referential Example 1, to prepare a hair-growing tonic (Composition 4).

EXAMPLE 5

The same process as in Example 1 was repeated, except that Compound 5 as obtained in Referential Example 3 was used in place of Compound 1 as obtained in Referential Example 1, to prepare a hair-growing tonic (Composition 5).

EXAMPLE 6

The same process as in Example 1 was repeated, except that Compound 6 as obtained in Referential Example 4 was used in place of Compound 1 as obtained in Referential Example 1, to prepare a hair-growing tonic (Composition 6).

EXAMPLE 7

The same process as in Example 1 was repeated, except that Compound 7 as obtained in Referential Example 5 was used in place of Compound 1 as obtained in Referential Example 1, to prepare a hair-growing tonic (Composition 7).

EXAMPLE 8

The same process as in Example 1 was repeated, except that Compound 8 was used in place of Compound 1 as obtained in Referential Example 1, to prepare a hair-growing tonic (Composition 8).

EXAMPLE 9

Seven kg of ethyl alcohol, 100 g of Compound 2, 50 g of isostearyl N-acetylglutamine, 10 g of dl-$\alpha$-tocopherol, 10 g of ascorbyl palmitate, 5 g of d-biotin, 0.1 g of $\beta$-carotene, 10 g of citric acid and 1790 g of pure water were uniformly stirred and blended thereby making the solids dissolved to prepare Solution A.

Apart from this, 1 kg of 1,3-butylene glycol and 25 g of POE (25) glyceryl pyroglutamate isostearate were uniformly stirred and blended to prepare Solution B. Solution B was added to Solution A with stirring and uniformly blended to prepare a hair-growing tonic (Composition 9). The above-mentioned operations were conducted all at room temperature, and the pH value of the solutions was adjusted at 4 by adding thereto a solution of sodium hydroxide.

REFERENTIAL EXAMPLE 1

Method of producing epicatechin-(4β→8)-catechin [Compound 1]:

1.25 kg of dry powder of seeds of betel nuts (*Areca catachu* L.) was extracted with 2 liters of 50 (v/v) % acetone [(v/v) % indicates a percentage by volume of acetone in water relative to the aqueous solution thereof—the same shall apply hereinunder], at room temperature for 2 hours. The resulting crude extract was filtered through filter paper (No. 526, produced by Advantec Toyo Co.) to obtain an extract. 1.5 liters of 50 (v/v) % acetone was again added to the residue to extract it at room temperature for one hour. The filtrates thus obtained by these operations were combined and concentrated under a reduced pressure. The resulting concentrate was passed through a column (having a size of 6 cmφ×44 cm and a volume of 1243 ml) as filled with Diaion HP-20 resin (produced by Mitsubishi Kasei Corp.) that had been equilibrated with 10 (v/v) % methanol, and then washed with 2.5 liters of 10 (v/v) % methanol. Next, 2.5 liters of 30 (v/v) % methanol and 1.25 liters of 30 (v/v) % methanol were applied to the column in that order, by which the intended fraction was eluted. The thus-obtained eluate was concentrated under a reduced pressure and then passed through a column (having a size of 9 cmφ×41 cm and a volume of 2607 ml) as filled with Sephadex LH-20 (produced by Pharmacia Co.) that had been equilibrated with 50 (v/v) % methanol, which was then washed with 5.2 liters of 50 (v/v) % methanol and 2.6 liters of 75 (v/v) % methanol. Next, 1.3 liters of 75 (v/v) % methanol was applied to the column, by which the intended fraction was eluted. The eluate was dried, and 3.75 g of a dry solid was obtained. The dry solid was dissolved in demineralized water and then subjected to partitioning high-performance liquid chromatography (using ODS column of 10 cmφ×100 cm, produced by YMC Co.) to obtain 0.5 g of Compound 1. The identification of Compound 1 thus obtained was effected by comparing the retention time of the compound in liquid chromatography and the Rf value thereof in thin-layer silica gel chromatography with those of the corresponding standard [see Journal of Chemical Society Chemical Communication, page 781, 1981].

REFERENTIAL EXAMPLE 2

Method of producing catechin-(4α→8)-catechin [Compound 3]:

Ten kg of powdered bran (powdered husks) of seeds of Nijo barley (*Hordeum vulgare* L. var. *distichon alefeld*) was extracted with 30 kg of 70 (w/w) % acetone [(w/w) % indicates a percentage by weight of acetone in water relative to the aqueous solution thereof], at room temperature for 4 days. The resulting crude extract was filtered through filter paper (No. 526, produced by Advantec Toyo Co.) to obtain 18.4 kg of an extract. The solvent was removed from the resulting filtrate, which was then dissolved in demineralized water. The resulting solution was passed through a column (having a size of 10 cmφ×50 cm and a volume of 3925 ml) as filled with Diaion HP-20 resin (produced by Mitsubishi Kasei Corp.) that had been equilibrated with water, which was then washed with 8 liters of 20 (v/v) % methanol and 8 liters of 40 (v/v) % methanol in that order. After this, 8 liters of 60 (v/v) % methanol was applied to the column, by which the intended fraction was eluted. The thus-obtained eluate was dried, and the resulting dry solid was dissolved in 0.1 liter of 25 (v/v) % methanol. Next, this was passed through a column (having a size of 6 cmφ×35 cm and a volume of 989 ml) as filled with Sephadex LH-20 that had been equilibrated with demineralized water, which was then washed with 2 liters of demineralized water and 2 liters of 50 (v/v) % methanol. Next, 2 liters of 75 (v/v) % methanol was applied to the column, by which the intended fraction was eluted. The eluate was dried, and 0.65 g of a dry solid was obtained. The dry solid was dissolved in demineralized water and then subjected to partitioning high-performance liquid chromatography (using ODS column of 2 cmφ×25 cm, produced by GL Science Co.) to obtain 0.23 g of Compound 3. The identification of Compound 3 thus obtained was effected by comparing the retention time of the compound in liquid chromatography and the Rf value thereof in thin-layer silica gel chromatography with those of the corresponding standard [see Journal of the Science of Food Agriculture, 34, 62].

REFERENTIAL EXAMPLE 3

Method of producing epicatechin-(4β→8)-epicatechin (4β→8)-epicatechin [Compound 5]:

21.6 liters of apple juice was passed through a column (having a size of 9 cmφ×50 cm and a volume of 3179 ml) as filled with Diaion HP-20 resin (produced by Mitsubishi Kasei Corp.) that had been equilibrated with water, which was then washed with 9 liters demineralized water and 2 liters of methanol. Next, one liter of methanol was applied to the column, by which the intended fraction was eluted. The resulting eluate was concentrated under a reduced pressure and again passed through a column (having a size of 7.2 cmφ×48 cm and a volume of 1953 ml) as filled with Diaion HP-20 resin (produced by Mitsubishi Kasei Corp.) that had been equilibrated with water, which was then washed with 4 liters demineralized water, 4 liters of 20 (v/v) % methanol and 4 liters of 30 (v/v) % methanol in that order. After this, 4 liters of 40 (v/v) % methanol was applied to the column, by which the intended fraction was eluted. From the resulting eluate, obtained was 6.1 g of a dry solid. Next, this was dissolved in 50 ml of 25 (v/v) % methanol, and the resulting solution was passed through a column (having a size of 3.4 cmφ×30 cm and a volume of 272 ml) as filled with Sephadex LH-20 that had been equilibrated with 25 (v/v) % methanol, which was then washed with 500 ml of 25 (v/v) % methanol and 500 ml of 50 (v/v) % methanol in that order. Next, 500 ml of 75 (v/v) % methanol was applied to the column, by which the intended fraction was eluted. From the resulting eluate, obtained was 1.5 g of a dry solid. The dry solid was dissolved in demineralized water and then subjected to partitioning high-performance liquid chromatography (using ODS column of 2 cmφ×25 cm, produced by GL Science Co.) to obtain 0.16 g of Compound 5. The identification of Compound 5 thus obtained was effected by comparing the retention time of the compound in liquid chromatography and the Rf value thereof in thin-layer silica gel chromatography with those of the corresponding standard [see Journal of Liquid Chromatography, 15, 637 (1992)].

REFERENTIAL EXAMPLE 4

Method of producing catechin-(4α→8)-catechin-(4α→8)-catechin [Compound 6]:

Huskless seeds of Nijo barley (*Hordeum vulgare* L. var. *distichon alefeld*) were dried by aeration, and 10 kg of the thus-dried seeds were ground with a Wiley mill (W-140 Model, produced by Ikeda Rika KiKi Co.). 50 liters of 75 (v/v) % acetone was added to this, which was thus extracted for 3 hours with stirring. The resulting crude extract was filtered through filter paper (No. 526, produced by Advantec Toyo Co.) to isolate a filtrate. Six kg of sodium chloride was added to the filtrate to make it saturated. After left as it was for 30 minutes, the separated acetone layer was collected. The acetone phase was concentrated under a reduced pressure to obtain 111 g of a dry solid. Next, the dry solid was dissolved in 500 ml of methanol and then passed through a column (having a size of 12 cmφ×44 cm and a volume of 4974 ml) as filled with Sephadex LH-20 that had been equilibrated with methanol, which was then washed with 10 liters of methanol. After this, 2.5 liters of methanol was applied to the column, by which the intended fraction was eluted. From the resulting eluate, obtained was 3.2 g of a dry solid. The dry solid was dissolved in demineralized water and then subjected to partitioning high-performance liquid chromatography (using ODS column of 2 cmφ×25 cm, produced by GL Science Co.) to obtain 0.31 g of Compound 6. The physico-chemical properties of Compound 6 are shown below.

TABLE 1

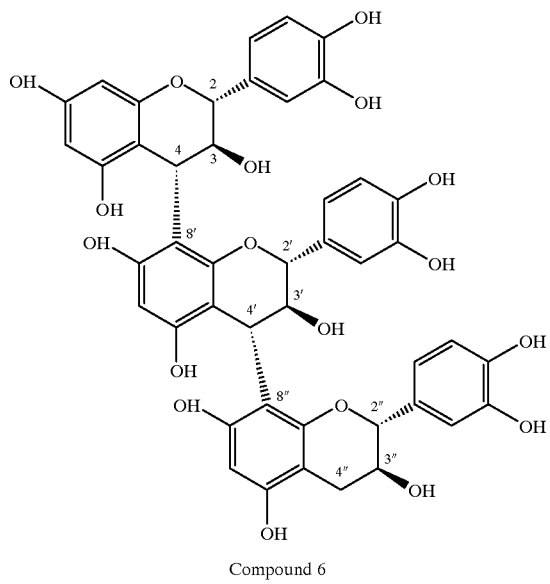

Compound 6

NMR of Compound 6

| Pos. No. | $^1$H NMR/CD$_3$OD (δ) | $^{13}$C NMR/CD$_3$OD (δ) |
|---|---|---|
| 2 | 4.3, 4.4 | 83.64, 89.71, 83.94, 85.52 |
| 3 | 4.4, 4.5 | 72.78, 72.97, 73.35, 73.97, 74.90 |
| 4 | 4.3, 4.4 | 38.96, 38.74, 39.12 |
| 2' | 4.2 | 83.64, 89.71, 83.94, 85.52 |
| 3' | 4.8 | 72.78, 72.97, 73.35, 73.97, 74.90 |
| 4' | 4.4 | 38.96, 38.74, 39.12 |
| 2" | 4.57, 4.72 | 83.03, 83.27 |
| 3" | 3.91, 4.06 | 68.55, 68.99 |
| 4" | 2.4–2.9 | 28.50, 28.90 |

Fab-MS (m/z); 867.1 (M + H)$^+$

REFERENTIAL EXAMPLE 5

Method of producing epicatechin-(4β→8)-epicatechin-(4β→8)-catechin [Compound 7]:

Compound 7 was produced in the manner mentioned below, according to the method described in Chemical and Pharmaceutical Bulletin, 50, 889 (1992).

Betel nuts (*Areca catachu* L.) were harvested, quartered and dried in an air drier at 40° C. for 3 days. The dried seeds were finely pulverized with a hammer and ground with a Wiley mill (W-140 Model, produced by Ikeda Rika KiKi Co.). 0.5 kg of the resulting dry powder was extracted with one liter of 50 (v/v) % acetone at room temperature for 3 hours. The resulting crude extract was filtered through filter paper (No. 526, produced by Advantec Toyo Co.) to obtain an extract. One liter of 50 (v/v) % acetone was again added to the residue, which was thus extracted at room temperature for 3 hours. The filtrates obtained by these operations were combined and concentrated under a reduced pressure. Demineralized distilled water was added to this to make 0.5 liters. 0.5 liters of ethyl acetate was added thereto to make it partitioned, and the thus-partitioned ethyl acetate layer was collected. This operation was repeated three times. All the ethyl acetate layers thus collected were combined and concentrated under a reduced pressure. 0.5 liter of demineralized distilled water was added thereto to give an aqueous suspension. Next, 0.5 liters of hexane was added thereto to make it partitioned. This operation was repeated twice. Then, the aqueous layer was collected and concentrated under a reduced pressure. The dry solid thus obtained was dissolved in 250 ml of demineralized distilled water, 250 ml of chloroform-methanol-water (3:3:2) mixture was added thereto, mixed and stirred, and the resulting mixture was then centrifuged at 3000 g for 20 minutes. The water-methanol layer (lower layer) was collected and concentrated under a reduced pressure. The resulting concentrate was passed through a column (having a size of 6 cmφ×29 cm and a volume of 8204 ml) as filled with Diaion HP-20 resin that had been equilibrated with water, which was then washed with 1.6 liters of water and 1.6 liters of 20 (v/v) % methanol in that order. Next, 1.6 liters of 40 (v/v) % methanol and 0.8 liters of 60 (v/v) % methanol were applied to the column in that order, by which the intended fraction was eluted. The resulting eluate was concentrated under a reduced pressure to obtain 8.8 g of a dry solid. Next, the dry solid was dissolved in 50 ml of demineralized water and passed through a column (having a size of 4 cmφ×29 cm and a volume of 820 ml) as filled with Sephadex LH-20 (produced by Pharmacia Co.) that had been equilibrated with water, which was then washed with 0.6 liters of water, 0.6 liters of 25 (v/v) % methanol, 0.3 liters of 50 (v/v) % methanol and 0.3 liters of 75 (v/v) %methanol in that order. After this, 0.3 liters of 75 (v/v) % methanol was applied to the column, by which the intended fraction was eluted. The resulting eluate was dried under a reduced pressure to obtain 0.95 g of Compound 7. The physico-chemical properties of Compound 7 are shown below.

TABLE 2

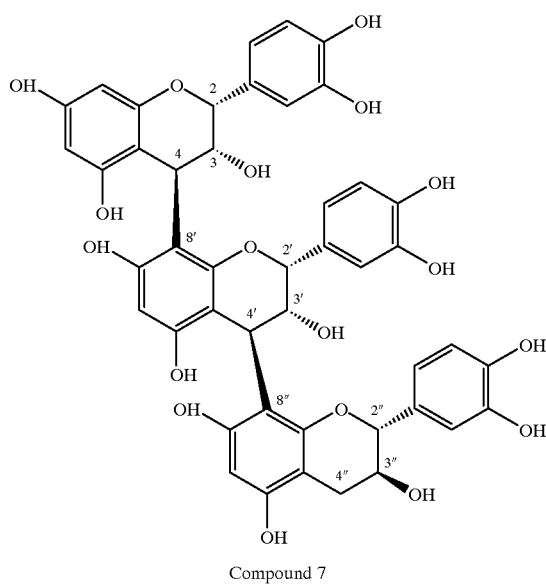

Compound 7

$^{13}$C NMR of Compound 7

| Pos. No. | acetone-$d_6$ + $D_2O$ (δ) | $CD_3OD$ (δ) |
|---|---|---|
| 2 | 75.8 | 77.07, 77.19 |
| 3 | 71.4–72.1 | 72.29, 73.40 |
| 4 | 35.9–36.5 | 37.34 |
| 2' | 75.8 | 77.07, 77.19 |
| 3' | 71.4–72.1 | 72.29, 73.40 |
| 4' | 35.9–36.5 | 37.34 |
| 2" | 80.47 | 82.06 |
| 3" | 66.61 | 68.29 |
| 4" | 26.10 | 26.90 |

Fab-MS (m/z); 867.2 (M + H)$^+$

TEST EXAMPLE 1

Test for Hair-Growing Effect in Mice:

With reference to the method of Ogawa et al. [see The Journal of Dermatology, 10, 45 (1983)], a test for the hair-growing effect in mice was carried out. In this test, used were 9-weeks-age male C3H/HeS1c mice of which the hair cycle was at the resting stage. The mice were grouped into plural groups and one group was comprised of 4 or 5 mice. The hair on the back of each mouse was shaven with an electric shaver. 150 µl of any of Compositions 1 to 8 as produced in Examples 1 to 8, respectively, was uniformly applied to the shaven area, once a day. To the mice in the control group, a tonic base having the same composition as the tonic preparation of each example but not containing proanthocyanidin was applied. On the 17th day in the test, the skin was peeled from the back of each mouse and photographed. The photographic pictures were processed with an imaging device (Spicca II Model, produced by Nippon Avionics Co.), from which was obtained the ratio of the haired area to the whole area of the tested skin. On the basis of the ratio thus obtained, the hair-growing effect of the tested tonic composition was evaluated. The results are shown in Table 3.

TABLE 3

| Composition | Percentage of Haired Area (%) |
|---|---|
| Composition 1 | 93 |
| Composition 2 | 98 |
| Composition 3 | 97 |
| Composition 4 | 90 |
| Composition 5 | 90 |
| Composition 6 | 93 |
| Composition 7 | 88 |
| Composition 8 | 84 |
| Control | 42 |

TEST EXAMPLE 2

Test for Stimulation of the Eyes of Rabbits:

New Zealand white rabbits (male, having a weight of from 3 to 3.5 kg) were used. 100 µl of a test solution as prepared by dissolving any of Compositions 1 to 8 of the invention as obtained in Examples 1 to 8, respectively, in pure water at a concentration of 5% was applied to the eyes of each rabbit. The test animals, rabbits were grouped into two groups. Five minutes after the application of the test solution thereto, the eyes of the rabbits of Group 1 were washed with running water. 24 hours after the application of the test solution thereto, the eyes of the rabbits of Group 2 were washed with running water. Only pure water was applied to the rabbits of the control group. One, 24, 48 and 72 hours and 7 days after the start of the test, the eyes of the rabbits were observed, resulting in that any clinical disorders of the eyes, such as keratoleukoma, iridemia, chemotic rubefaction, discharge from the eyes, etc. were not found in all the tested rabbits.

TEST EXAMPLE 3

Test of Continuous Application to the Skin of Rabbits:

New Zealand white rabbits (male, 22-weeks-age) were used. The hair on the back of each rabbit was shaven, and any of Compositions 1 to 8 of the invention as produced in Examples 1 to 8, respectively, was applied to the shaven area, once a day and continuously for 3 months, whereupon the stimulation of the skin, if any, was checked. Precisely, the rabbits were grouped into 4 test groups, and 200 µl of the test liquid was applied to about 15 cm$^2$ (5 cm×3 cm) of the shaven area of each rabbit. Two control groups were prepared. A proanthocyanidin-free tonic liquid was applied to the rabbits of one control group, while nothing was applied to those of the other control group. As a result of the test, any clinical disorders of the skin, such as inflammation, rubefaction, etc., were not found in all the rabbits of both the test groups and the control groups.

TEST EXAMPLE 4

Clinical Test on Human Patients:

(1) Method of Clinical Test:

This is to evaluate the effectiveness of the composition of the present invention for male pattern baldness. A tonic comprising Composition 9 as obtained in Example 9 was used as the test substance. This was applied to 37 volunteer panelists to test the clinical effect of Composition 9. The volunteer panelists were men of from 25 to 60 years old, who were all healthy except that they had male pattern baldness on the head. As the control substance, used was a tonic having the same composition as Composition 9 except that it did not contain Compound 2.

Precisely, these 37 volunteer panelists were impartially grouped into two groups, irrespective of the background factors such as the age, the condition of the baldness, the type of the baldness, etc., one group being comprised of 19 panelists while the other being comprised of 18 panelists. The test substance was applied to the 19 panelists of the former group (test group), and the control substance was applied to the 18 panelists of the latter group (control group). During the test that lasted for 24 weeks, from 1.5 to 2 ml of the test substance (Composition 9) or the control substance was applied to the affected area of the head of each panelist, every day once in the morning and at night.

(2) Method of Evaluation:

The effectiveness of the test substance in the clinical test was evaluated by four methods, dermatological diagnosis, photographic decision, measurement of the thickness of the hair, and measurement of the density of the hair. The outline of each method is mentioned below.

i. Dermatological Diagnosis:

Before and after the test, the part to which the test or control tonic had been applied was examined by a dermatologist with respect to the degree of baldness, the degree of hard hair grown and the degree of soft hair grown. After having been totally checked in that manner, the panelists were ranked in four ranks (significantly cured, cured, not cured, worsened) whereby the effect of the tonic tested was evaluated. In addition, the part to which the test or control tonic had been applied was also examined as to whether or not it had side effects of inflammation, etc.

ii. Photographic Decision:

Before and after the test, the head of each panelist was photographed at the top and the back. The photographic pictures were used as reference data for the clinical diagnosis of the baldness and for the examination of the growing hair. On the basis of these pictures, the panelists were ranked in four ranks as above whereby the effect of the tonic tested was evaluated.

iii. Thickness of Hair:

Before and after the test, the hair was collected from a predetermined site of the head of each panelist, and the thickness of the base of the hair was measured. From the change in the thickness of the base of the hair, the panelists were ranked in three ranks (thickened, not changed, thinned) whereby the effect of the tonic tested was evaluated.

iv. Density of Hair:

Before and after the test, the density of the hair in the site, from which the hair was collected for the previous iii, was measured. For the measurement, used was an enlarged photograph of the head of each panelist. From the change in the density of the hair, the panelists were ranked in three ranks (increased, not changed, decreased) whereby the effect of the tonic tested was evaluated.

(3) Results:

The results of the dermatological diagnosis, the photographic decision, the measurement of the thickness of the hair and the measurement of the density of the hair are shown in Table 4. In the dermatological diagnosis, no side effect of the tonic tested was observed.

TABLE 4

| Method of Evaluation | Results | Groups of Panelists | |
|---|---|---|---|
| | | Group to which control tonic was applied (%) | Group to which test tonic was applied (%) |
| i. Dermatological Diagnosis | Significantly cured | 11.1 | 26.3 |
| | Cured | 22.2 | 31.6 |

TABLE 4-continued

| Method of Evaluation | Results | Groups of Panelists | |
|---|---|---|---|
| | | Group to which control tonic was applied (%) | Group to which test tonic was applied (%) |
| | Not cured | 66.7 | 42.1 |
| | Worsened | 0 | 0 |
| ii. Photographic Decision | Significantly cured | 0 | 31.6 |
| | Cured | 11.1 | 21.1 |
| | Not cured | 88.9 | 47.4 |
| | Worsened | 0 | 0 |
| iii. Thickness of Hair | Thickened | 38.9 | 73.7 |
| | Not changed | 38.9 | 15.8 |
| | Thinned | 22.2 | 10.5 |
| iv. Density of Hair | Increased | 38.9 | 73.7 |
| | Not changed | 11.1 | 10.5 |
| | Decreased | 50.0 | 15.8 |

As seen from Table 4, the dermatological diagnosis revealed that 57.9% of the volunteer panelists, to whom had been applied the test tonic, was significantly cured or cured of the baldness (whereas 33.3% of the group to which control tonic was applied was significantly cured or cured); the photographic decision revealed that 52.7% of the volunteer panelists, to whom had been applied the test tonic, was significantly cured or cured of the baldness (whereas 11.1% of the group to which control tonic was applied, was cured); the measurement of the thickness of the hair revealed that the hair was thickened in 73.7% of the volunteer panelists, to whom had been applied the test tonic (whereas 38.9% of the group to which control tonic was applied was thickened); and the measurement of the density of the hair revealed that the density of the hair was increased in 73.7% of the volunteer panelists, to whom had been applied the test tonic (whereas 38.9% of the group to which control tonic was applied was increased).

Accordingly, the effect by administration of the compound of the present invention was verified in all the four test methods as described above.

TEST EXAMPLE 5

Acute Toxicity:

Compound 2 was subcutaneously administered to a group of five male dd mice (weight: 20±1 g) at a dose of 2000 mg/kg, resulting in that none of the mice died.

From the results of the test examples mentioned above, it has been verified that the hair-growing agent comprising proanthocyanidin of the present invention exhibits an excellent hair-growing effect and even an excellent hair-regrowing effect while having no stimulation to the eye and the skin and that it is safe and can be used even continuously for a long period.

INDUSTRIAL APPLICABILITY

The present invention is utilizable as a hair-growing agent comprising proanthocyanidin as the active ingredient.

What is claimed is:

1. A method for stimulating hair growth in a mammal, which comprises applying to the skin of said mammal a proanthocyanidin comprising at least one polymer selected from the group consisting of epicatechin-(4β→8)-catechin, epicatechin-(4β→8)-epicatechin, catechin-(4α→8)-catechin, epicatechin-(4β→6)-epicatechin, epicatechin- (4β→8)-epicatechin-(4β→8)-epicatechin, catechin-(4α→8)-catechin-(4α→8)-catechin, epicatechin-(4β→8)-epicatechin-(4β→8)-catechin and epicatechin-(4β→8)-epicatechin-(4β→6)-epicatechin, in an amount of 0.1 to 600 mg/adult/day until hair-growing is observed.

2. The method as claimed in claim 1, wherein said at least one polymer is selected from the group consisting of epicatechin-(4β→8)-epicatechin, catechin-(4α→8)-catechin and epicatechin-(4β→8)-epicatechin-(4β→8)-epicatechin.

3. The method as claimed in claim 1, wherein the proanthocyanidin is applied to the scalp of said mammal.

* * * * *